US012616438B2

(12) United States Patent
Crisman et al.

(10) Patent No.: US 12,616,438 B2
(45) Date of Patent: May 5, 2026

(54) ECHOGENIC NEEDLE

(71) Applicant: SMITHS MEDICAL ASD, INC., Plymouth, MN (US)

(72) Inventors: Andrew Crisman, Shoreview, MN (US); Alysa Lauren Granata, Minneapolis, MN (US)

(73) Assignee: ICU MEDICAL, INC., San Clemente, CA (US)

( * ) Notice: Subject to any disclaimer, the term of this patent is extended or adjusted under 35 U.S.C. 154(b) by 42 days.

(21) Appl. No.: 18/757,712

(22) Filed: Jun. 28, 2024

(65) Prior Publication Data

US 2024/0358347 A1 Oct. 31, 2024

Related U.S. Application Data

(62) Division of application No. 17/679,331, filed on Feb. 24, 2022, now Pat. No. 12,053,322, which is a (Continued)

(51) Int. Cl.
*A61B 8/08* (2006.01)
*A61M 5/32* (2006.01)
(Continued)

(52) U.S. Cl.
CPC .......... *A61B 8/0841* (2013.01); *A61B 8/0833* (2013.01); *A61B 2017/3413* (2013.01);
(Continued)

(58) Field of Classification Search
CPC ............... A61B 8/0841; A61B 8/0833; A61B 2017/3413; A61B 2090/3925; A61B 17/3403; A61M 5/329; A61M 19/00
See application file for complete search history.

(56) References Cited

U.S. PATENT DOCUMENTS 4,401,124 A * 8/1983 Guess ................. A61B 8/0833
600/458
5,718,676 A * 2/1998 Barrett ............... A61F 9/00745
604/272
(Continued)

FOREIGN PATENT DOCUMENTS

EP 0072671 A2 2/1983
EP 002789297 9/2014
(Continued)

OTHER PUBLICATIONS

PCT International Search Report and Written Opinion, Application No. PCT/US2016/057684, Jan. 31, 2017
(Continued)

*Primary Examiner* — Bayan Salone
(74) *Attorney, Agent, or Firm* — Louis Woo

(57) ABSTRACT

An echogenic needle may have at least one V-shaped spiral groove formed at its distal portion adjacent to its patient end. The walls of the groove are orthogonal to each other. The groove is titled at a given angle from a neutral position toward the proximal end of the needle so that when the needle is inserted into the patient at an insertion angle under ultrasound imaging, the ultrasound wave emitted from the ultrasound transducer is reflected in a substantially reverse direction back to the transducer by at least one wall of the spiral groove. A pair of crisscrossing grooves may be spirally wound about the distal portion of the needle with each groove being tilted to the given angle to enhance echogeneity. The echogeneity of the needle may also be enhanced by increasing the pitch density of each groove while maintaining the crisscrossing groves at their neutral position.

14 Claims, 4 Drawing Sheets

Related U.S. Application Data division of application No. 15/297,731, filed on Oct. 19, 2016, now Pat. No. 11,918,410.

(60) Provisional application No. 62/246,205, filed on Oct. 26, 2015.

(51) Int. Cl.
| | |
|---|---|
| *A61M 19/00* | (2006.01) |
| *A61B 17/34* | (2006.01) |
| *A61B 90/00* | (2016.01) |

(52) U.S. Cl.
CPC ...... *A61B 2090/3925* (2016.02); *A61M 5/329* (2013.01); *A61M 19/00* (2013.01)

(56) References Cited

U.S. PATENT DOCUMENTS

| | | | | |
|---|---|---|---|---|
| 5,766,135 | A * | 6/1998 | Terwilliger | A61B 8/0833 600/562 |
| 6,053,870 | A * | 4/2000 | Fulton, III | A61B 17/3421 600/458 |
| 8,398,596 | B2 * | 3/2013 | Field | A61B 90/39 604/164.05 |
| 8,617,079 | B2 | 12/2013 | Mitchell | |
| 9,521,993 | B2 * | 12/2016 | Ryan | A61B 17/3403 |
| 9,592,352 | B2 * | 3/2017 | Matsuzawa | A61M 5/329 |
| 9,872,666 | B2 * | 1/2018 | Quearry | A61B 8/4455 |
| 9,980,699 | B2 * | 5/2018 | Quearry | A61B 10/0233 |
| 12,053,322 | B2 * | 8/2024 | Crisman | A61B 8/0841 |
| 12,082,842 | B2 * | 9/2024 | Crisman | A61B 17/3415 |
| 2003/0158480 | A1 * | 8/2003 | Tornes | A61B 90/39 600/437 |
| 2009/0131734 | A1 * | 5/2009 | Neustadter | A61B 90/39 600/8 |
| 2010/0168684 | A1 * | 7/2010 | Ryan | A61B 17/3403 604/272 |
| 2010/0256577 | A1 | 10/2010 | Field | |
| 2012/0101380 | A1 * | 4/2012 | Blum | A61B 17/3401 600/437 |
| 2012/0253297 | A1 | 10/2012 | Matsuzawa | |
| 2013/0225997 | A1 * | 8/2013 | Dillard | A61B 10/0283 29/896.9 |
| 2014/0058268 | A1 * | 2/2014 | Mitchell | A61B 5/153 600/458 |
| 2014/0276073 | A1 | 9/2014 | Quearry | |
| 2014/0336687 | A1 * | 11/2014 | Iwase | B24B 19/028 451/28 |
| 2016/0074130 | A1 * | 3/2016 | Quearry | A61B 8/0841 600/424 |
| 2016/0120509 | A1 * | 5/2016 | Syed | A61B 17/3403 600/458 |
| 2017/0043100 | A1 * | 2/2017 | Nguyen | A61B 17/3417 |
| 2022/0175342 | A1 * | 6/2022 | Crisman | A61B 8/0841 |
| 2023/0131115 | A1 * | 4/2023 | Halmann | A61B 8/481 600/424 |
| 2024/0358347 | A1 * | 10/2024 | Crisman | A61B 8/0833 |

FOREIGN PATENT DOCUMENTS

| | | | | | |
|---|---|---|---|---|---|
| FR | 2272633 | A1 * | 12/1975 | | |
| JP | 2000051219 | A * | 2/2000 | | |
| JP | 2006101915 | A * | 4/2006 | | |
| JP | 2010194013 | A * | 9/2010 | | |
| WO | WO-2014133936 | A1 * | 9/2014 | | A61B 8/488 |
| WO | WO-2014149821 | A1 * | 9/2014 | | A61B 8/0841 |

OTHER PUBLICATIONS

EP Search Report dated Sep. 1, 2022 cited in EP Application No. 22176413.7.

* cited by examiner

ECHOGENIC NEEDLE

This application is a divisional of, and claims priority from, application Ser. No. 17/679,331 filed on Feb. 24, 2022. The '331 application in turn claims priority from application Ser. No. 15/297,731 filed on Oct. 19, 2016 claiming priority from provisional application No. 62/246,205 filed on Oct. 26, 2015. The disclosures of application Ser. Nos. 17/679, 331 and 15/297,731 in their entirety are hereby incorporated by reference.

FIELD OF THE INVENTION

The present invention relates to echogenic medical devices, and more particularly a needle that may be used for peripheral nerve block (PNB) procedures having echogenic features at its patient end.

BACKGROUND OF THE INVENTION

There are numerous echogenic needles known. Among them is the Wallace Amniocentesis Needles that are being sold by the assignee of the instant invention. The instant invention aims to improve the echogeneity of the echogenic features of needles use for different surgical procedures including peripheral nerve block (PNB), epidural and others that require ultrasound viewing of the needle during the procedure.

SUMMARY OF THE PRESENT INVENTION

The echogenic needle of the instant invention has at its distal portion adjacent its patient end at least one section that has a spiral V-shaped groove. The walls of the groove are orthogonal to each other. The groove may be tilted at a given angle from its neutral position toward the proximal end of the needle. The inventive needle is usually inserted into a subject patient at a desirable insertion angle. If the needle is under ultrasound imaging whereby an ultrasound wave is directed to the needle, at least one wall of the tilted groove would reflect the ultrasound wave back to the receiver of the transducer at substantially the reverse direction, i.e., at approximately 180°, to present an improved ultrasound image of the echogenic needle. Also, by decreasing the pitch between the adjacent tips formed by the V-shaped groove, the density of the number of turns for the groove increases. As a result, an enhanced ultrasound wave is reflected back to the receiver of the transducer to provide an improved image of the echogenic needle, even were the groove not tilted at the aforenoted given angle.

In one embodiment, by forming the echogenic groove in a spiral fashion, while maintaining the preferred tilt angle to the groove, the echogenic needle of the instant invention may be made simply. Moreover, that the walls of the groove are orthogonal to each other means that the only angle that needs to be adjusted with regard to the production of the echogenic needle is the tilt angle, which may simply be done by adjusting either the angle of the needle shaft that is being cut, or the angle of the cutting wheel or tool used to cut the groove as the needle shaft is rotatably moved relative to the cutting wheel, which may also be rotating. In an other embodiment, the pitch (of the sidewalls) of the groove is further decreased so as to increase the pitch density for the spiral groove to a range that leads to an improved reflection of the ultrasound image. For the other embodiment, there may not be a need to tilt the groove.

Instead of one spiral groove, the echogenic section of the needle may be made with two crisscrossing spiral grooves, i.e., one clockwise and one counter-clockwise relative to the sharp tip of the needle. Each of the V-shaped grooves has walls that are orthogonal to each other. Furthermore, the grooves each may be tilted at a predetermined angle relative to the proximal end of the needle to effect a substantially 180° reflection of the ultrasound wave from the transducer back to the transducer, when the needle is positioned at an insertion angle that facilitates the insertion of the needle into the subject patient.

Instead of one echogenic section, the distal portion of the needle shaft may have a plurality of echogenic sections. For the exemplar embodiments, the needle shaft may have two echogenic sections separated by a non-groove section, so that there are two sections of crisscrossing spiral grooves each adapted to be tilted at a predetermine angle to reflect the ultrasound wave emitted from a transducer back to the transducer. In the other embodiment, the crisscrossing spiral sections are not tilted. Accordingly, the walls of each of the spiral grooves would have the same length while substantially orthogonal to each other.

The instant invention is therefore directed to a needle for viewing under ultrasound imaging that comprises a shaft extending along a longitudinal axis having a proximal end and a distal end including a sharp tip, one and other grooves spirally formed clockwise and counterclockwise, respectively, from at least adjacent the sharp tip along a distal portion of the shaft so that the one and other grooves crisscross each other a predetermined distance along the distal portion, the one and other grooves each being at a neutral position relative to the longitudinal axis of the shaft, each of the one and other grooves has an increased pitch density in a range that enhances the reflection of the ultrasound wave from an ultrasound transducer directed to the shaft as an improved reflection image back to the transducer. The walls of each of the grooves are orthogonal to each other and have the same length.

The present invention is further directed to a needle for viewing under ultrasound imaging that comprises a shaft extending along a longitudinal axis having a proximal end and a distal end including a sharp tip, one groove formed spirally from at least adjacent the sharp tip a predetermined distance along the shaft away from the sharp tip, the one groove being tilted from a neutral position to a tilt angle position toward the proximal end of the shaft so that an ultrasound wave from an ultrasound transducer directed to the shaft is reflected in a substantially reverse direction back to the transducer by at least a wall of the one groove when the shaft is positioned at an insertion angle for insertion into a subject.

The present invention is moreover directed to a needle for viewing under ultrasound imaging that comprises a shaft extending along a longitudinal axis having a proximal end and a distal end including a sharp tip, one and other grooves spirally formed clockwise and counterclockwise, respectively, from at least adjacent the sharp tip along a distal portion of the shaft so that the one and other grooves crisscross each other a predetermined distance along the distal portion, each of the one and other grooves being tilted from its neutral position to a tilt angle position toward the proximal end of the shaft so that an ultrasound wave from an ultrasound transducer directed to the shaft is reflected in a substantially reverse direction back to the transducer by at least a wall of each of the one and other grooves when the shaft is positioned at an insertion angle for insertion into a subject.

BRIEF DESCRIPTION OF THE FIGURES

The present invention will become apparent and the invention itself will be best understood with reference to the following description of the present invention taken in conjunction with the accompanying drawings, wherein.

DETAILED DESCRIPTION OF THE INVENTION

Figures 1, 2:
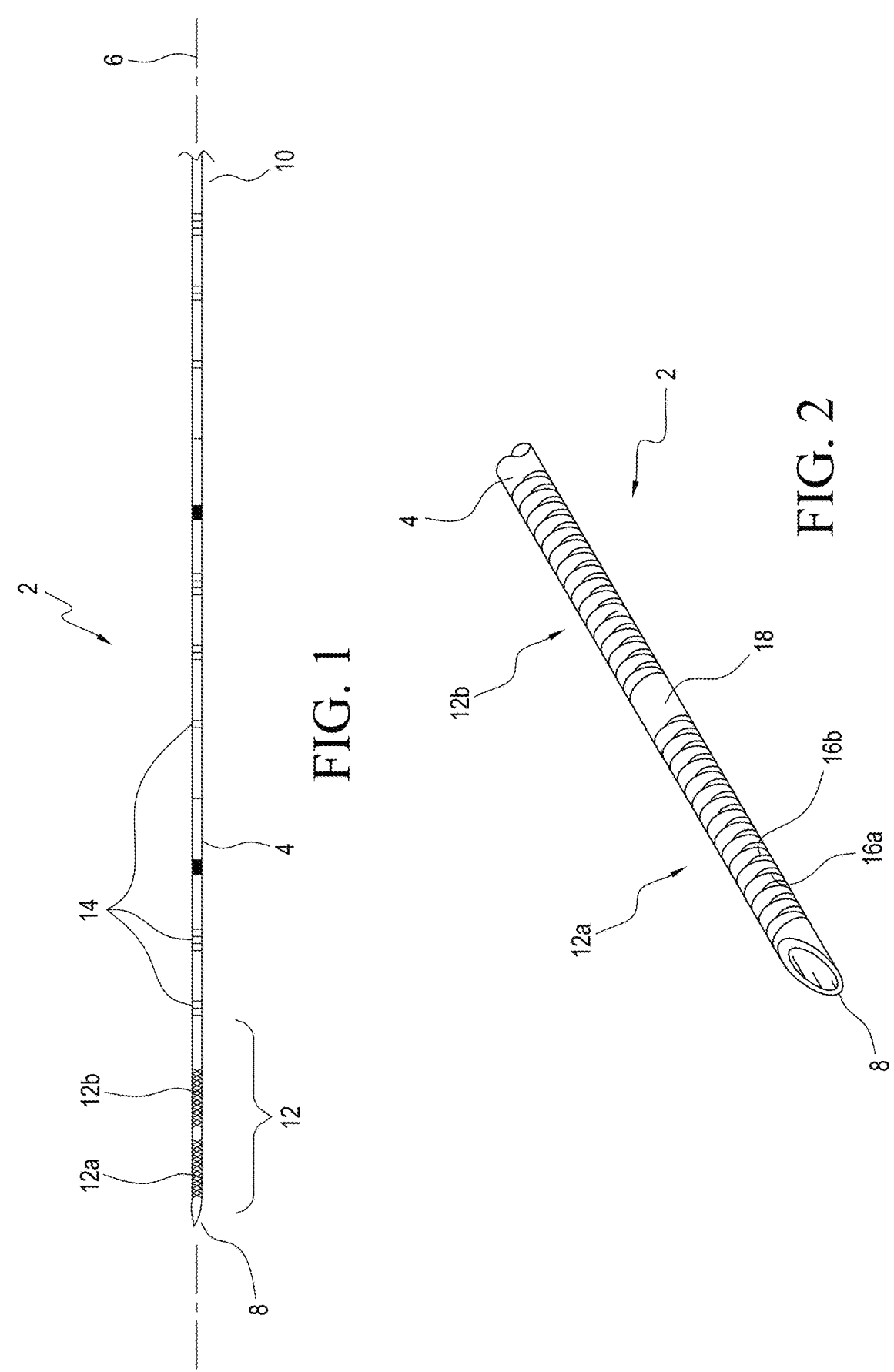
FIG. 1 is an overall illustration of the exemplar embodiments of the needle of the instant invention.
FIG. 2 is an enlarged view of the distal portion of the needle of FIG. 1.

An exemplar embodiment of the inventive needle used, for example for peripheral nerve block procedures, is shown in FIG. 1. As shown, needle 2 has a shaft 4 that extends along a longitudinal axis 6 having a distal or patient end 8 including a sharp bevel tip and a proximal end 10. For ease of illustration, the proximal end 10 of needle 2 has been truncated in FIG. 1. The section of the needle that is adjacent to patient end 8 is designated distal portion 12, although it should be appreciated that the demarcation of distal portion 12 as shown in FIG. 1 is for discussion only. Beyond distal portion 12 there are a number of markings 14 along the shaft of the needle to show the length, or the depth of the needle, as the needle is inserted into the subject, or patient. There are two sections 12a and 12b at the distal portion that are better illustrated in the enlarged distal portion view of the needle in FIG. 2.

Figures 3, 4, 5A, 5B:
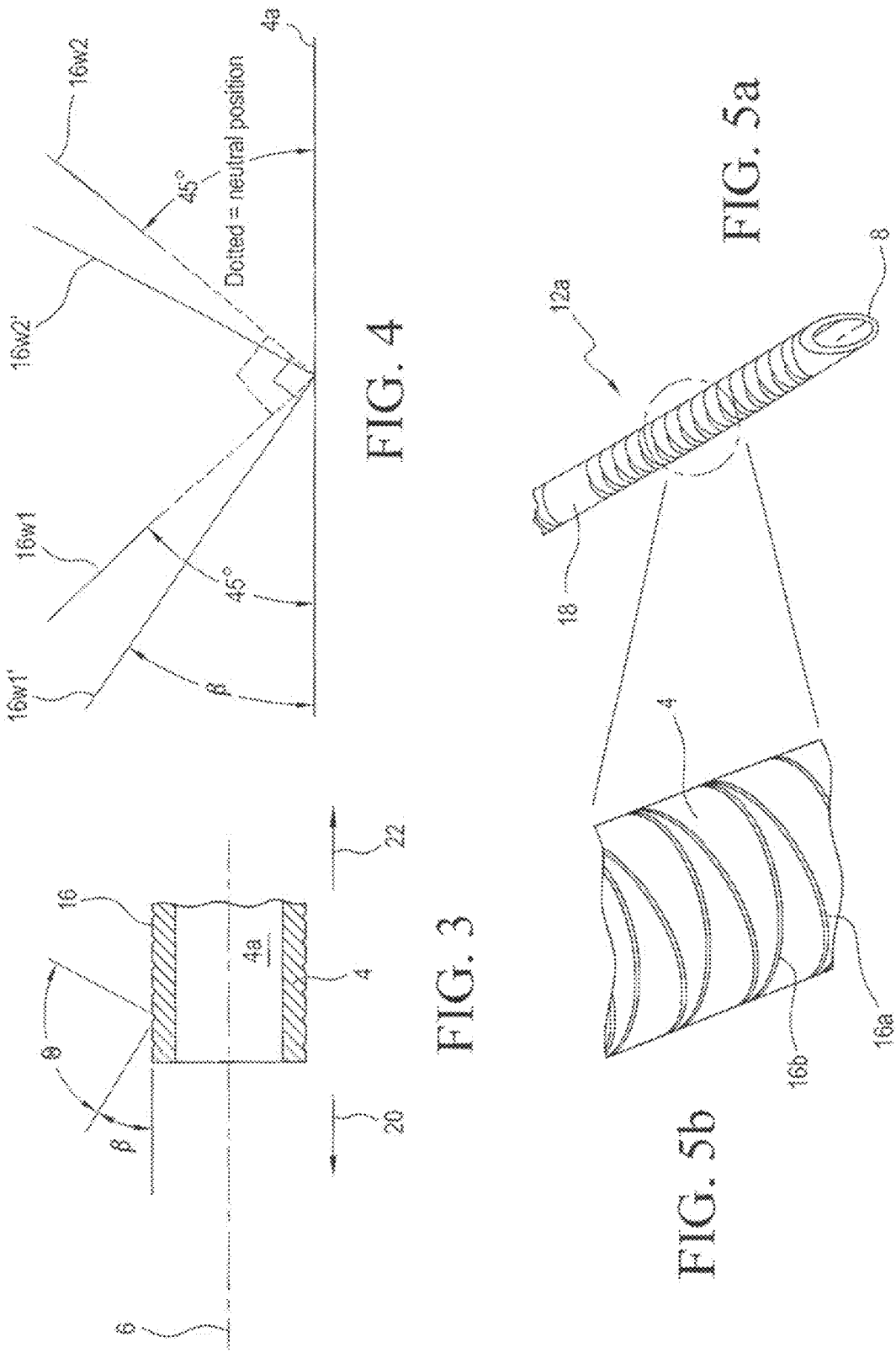
FIG. 3 is a cross-sectional view of a section of an exemplar groove of the needle of FIG. 1.
FIG. 4 is a cross-sectional view of the exemplar groove showing its neutral position and its "tilted" angle position.
FIG. 5A shows the patient end of the exemplar needle shown in FIG. 1.
FIG. 5B is an enlarged view of a portion of the exemplar needle of FIG. 5A showing crisscrossing spiral grooves.

As shown in FIG. 2, sections 12a and 12b each are formed with crisscrossing spiral grooves that are also shown in FIG. 5B. With reference to FIGS. 2, 5A and 5B, one spiral groove 16a is formed on the outer circumferential wall of needle shaft 4 in one direction, for example a clockwise direction, while an other spiral groove 16b crisscrosses groove 16a in an other direction, for example a counter-clockwise direction. For ease of reference, the respective grooves 16a and 16b spiral about the outer circumferential wall of needle shaft 4 may be referenced with respect to the sharp bevel tip at patient end 8 of the needle. Thus, for the discussion hereinbelow, groove 16a may be considered to be a spiral groove that is formed on the outer circumferential wall of needle shaft 4 in a clockwise direction relative to needle tip 8, while groove 16b spirally wounds about the outer circumferential wall of needle shaft 4 in a counter-clockwise direction relative to needle tip 8. The two spiral grooves crisscross each other in the manner as shown in FIGS. 2, 5A and 5B.

As best shown in FIG. 2, there is a non-groove section 18 that separates grooved sections 12a and 12b at the distal portion of the exemplar inventive needle. Although two grooved sections are shown in FIGS. 1 and 2, it should be appreciated that a plurality of more than two groove sections may also be formed along the needle away from its patient end.

The configuration of the groove of the needle is illustrated in FIGS. 3-4 and 6A-6C. FIG. 3 shows a cross-section of the needle, for example a portion of section 12a, with directional needle 20 referencing the proximal end of the needle and directional needle 22 referencing the patient end of the needle. As shown in FIG. 3, a number of cross-sections of a groove 16 are shown to have formed on the outer circumferential wall of needle shaft 4, which has a passage 4a extending therethrough along longitudinal axis 6. For the exemplar illustration of FIG. 3, a $\Theta$ angle is shown to be formed between the two walls of the groove, represented by lines 16w1 and 16w2 in FIG. 4. As the walls are orthogonal to each other, the $\Theta$ angle formed between the two walls is assumed to be approximately 90°. Thus, were the spiral groove at the outer surface of the circumferential wall of shaft 4 to be formed to have its walls orthogonal to each other relative to the longitudinal axis of the needle so that the walls have the same length, then each of the walls 16w1 and 16w2 would extend at approximately 45° relative to a plane along the longitudinal axis of shaft 4. This is shown by the dotted lines in FIGS. 4 and 6C, and may be referred to as the neutral position of the groove.

The inventors have found that, in use, a clinician usually positions a needle at an angle that facilitates the insertion of the needle into the subject. Thus, were the groove "tilted" at a given angle α toward the proximal end of the needle, an improved reflection of an ultrasound wave directed by an ultrasound transducer towards the needle may be obtained. By empirical studies, it was found that the α angle may range from approximately 5° to 25°, and preferably at 10° relative to the neutral position. Thus, instead of 45° for each of the walls of the V-shaped groove, the "tilted" groove would have its walls, as designed by lines 16w1' and 16w2', shifted together such that wall 16w1' is at a β angle relative to the outside walls 4a of the needle shaft. Walls 16w1' and 16w2' remain orthogonal to each other when at the "tilted" position. For the exemplar embodiment where α=10°, β would be 35°. The depth of the groove may vary anywhere from 0.006 inch to 0.025 inch (0.1524 mm to 0.635 mm). It is further found that the pitch between grooves, as designated by reference number 24 in FIG. 6B, could be reduced to between 0.010 and 0.050 inch (0.254 mm to 1.27 mm), and preferably to approximately 0.020 inch (0.508 mm) to improve the pitch density of the needle and thereby its echogeneity. As should be appreciated, the pitch and groove as described above are not definitive for all needles but are instead meant to be utilized for needles that have conventionally dimensioned walls, for example a needle having a gauge anywhere between 16 to 24.

Figures 6A, 6B, 6C:
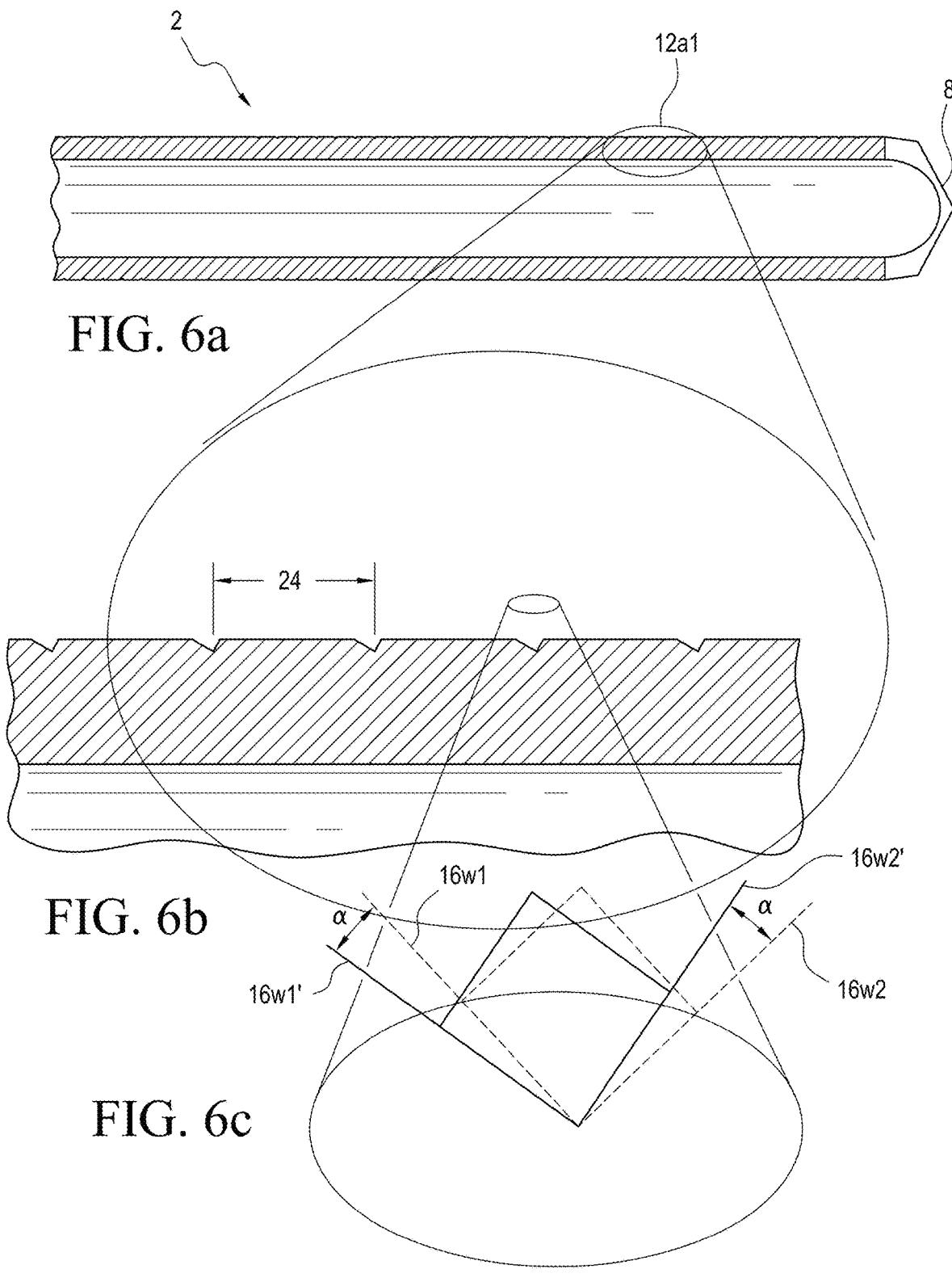
FIG. 6A is a cross-sectional view of a distal or patient end of an exemplar inventive needle.
FIG. 6B is an enlarged view of a portion of the wall of the needle of FIG. 6A showing more clearly a number of cross sections of the groove.
FIG. 6C is an enlarged cross-sectional view showing the two walls of a V-shaped groove at its neutral position and its tilted position.

The configuration of the exemplar embodiment of the echogenic needle of the instant invention is further shown in FIGS. 6A-6C where a portion 12a1 of groove section 12a is enlarged in FIG. 6B to show an enlarged cross-sectional view of a number of V-shaped cross sections of the groove tilted toward the proximal end of the needle as described above. FIG. 6C shows the neutral position (in dotted lines)

and the tilt angle position, or simply the tilted position (in solid lines) of the walls of an exemplar cross section of the V-shaped groove.

Figure 7:
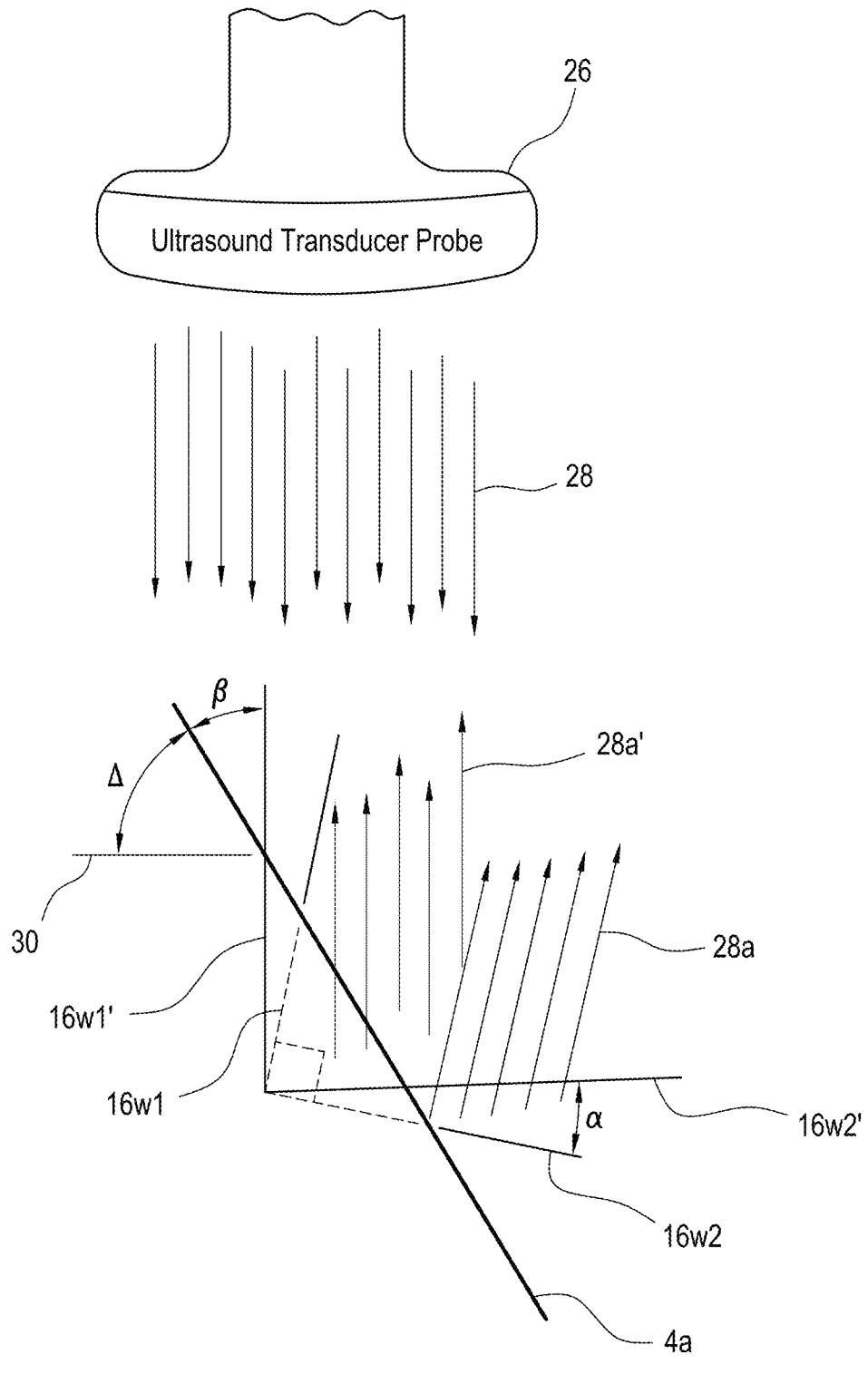
FIG. 7 is an illustration showing an ultrasonic wave emitted from an ultrasonic transducer to the needle, and the reflection of the ultrasound wave back to the transducer by the groove at the neutral position and at the tilt angle position.

FIG. 7 is an exemplar illustration showing the difference in the reflection of the ultrasound wave emitted by an ultrasound transducer toward the exemplar inventive needle. For ease of discussion, the exemplar needle of FIG. 7 is assumed to have only one spiral groove. As shown, the transmitter of ultrasound transducer probe 26 emits an ultrasound wave 28 toward needle shaft 4, represented by line 4*a*, which is presumably being inserted into a subject. Thus, needle 4 is at an insertion angle Δ with reference to a plane 30 that is assumed to be in parallel to the plane at the output surface of transducer 26. From empirical studies, it was found that Δ in most instances is between 50° and 60°, and preferably at approximately 55°. Thus, it was determined that with the V-shaped groove at the tilt angle α, the ultrasound wave 28 is reflected as ultrasound wave 28*a*' in a substantially reverse direction (approximately at 180°) back to transducer 26, presumably to its receiver. Thus, an improved reflection view of the exemplar inventive needle may be gleaned under ultrasound or radiographic imaging by tilting the groove at an angle α.

As discussed above, with the exemplar illustration as shown in FIG. 7, it was determined that if the spiral grooves were formed at their respective neutral positions, the ultrasound wave 28 would be reflected as a return ultrasound wave, represented by lines 28*a*, in a direction that angles away, or offset from ultrasound transducer 26. However, based on additional empirical studies, it has been determined that were the crisscrossing spiral grooves formed on a needle with their corresponding respective walls orthogonal to the longitudinal axis of the needle but with the pitch density for each of the spiral grooves increased more than as discussed above, an improved and acceptable reflective image of the echogenic portion(s) of the needle under ultrasound imaging is nonetheless achieved. In other words, spiral grooves formed in the neutral position relative to the longitudinal axis of the needle with a predetermined increased pitch density would provide an improved reflective image of the echogenic portion(s) of the needle, similar to the needle embodiment with the tilted grooves as discussed above.

The neutral positioned spiral grooves are represented by the dotted wall lines 16*w*1 and 16*w*2 in FIGS. 4 and 6C. Due to those spiral grooves being formed at the neutral position and orthogonal to each other, their walls, for example 16*w*1 and 16*w*2, have substantially the same length or height. The pitch, or the groove width, between the walls of each of the grooves, designated by 24 in FIG. 6, was determined to have a range approximately 0.001 inch to 0.003 inch (0.025 mm to 0.075 mm), and preferably at approximately 0.002 inch (0.053 mm). The desired groove depth was determined to have a range of approximately 0.0006 inch to 0.0010 inch (0.015 mm to 0.025 mm). As should be appreciated, the depth and pitch of the groove are interrelated as the change in the value of one may affect the change in the value of the other.

With the combination of clockwise and counter-clockwise spiral wound grooves, and with each of the grooves having a preferable pitch of approximately 0.020 inch (0.508 mm) for the tilted echogenic needle embodiment, an echogenic needle with improved echogeneity results. So, too, an improved echogenic needle adapted to provide improved echogeneity results may be achieved with non-tilted crisscrossing clockwise and counter-clockwise spiral grooves each having an increased pitch density or groove width having a range of 0.001 inch to 0.003 inch (0.025 mm to 0.075 mm), and preferably of approximately 0.0021 inch (0.053 mm). It should be appreciated that instead of a V-shaped groove, each of the grooves may be U-shaped or some other shape such as trapezoidal-shaped, so long as the walls of the groove are made to be substantially orthogonal to each other. Furthermore, one of the crisscrossing grooves may have a V-shape while the other groove may have a U-shape or some other shape including trapezoidal that clearly defines the orthogonal walls of the groove.

Although not disclosed above, it should be appreciated that the proximal end of the needle may be fixedly bonded or connected to a needle hub, so that the needle may be fluidly coupled to a medicament or fluid store, such as a syringe or a pump, to infuse medicament or fluid to the patient once the needle has been inserted into and appropriately positioned within the patient. The respective connectors of the needle hub and the fluid store may be configured to have complementary features or configurations that allow only those connectors to be coupled to each other, i.e., each of those connectors is not connectable to a counterpart conventional luer connector. Moreover, before use, the needle may be protected by a sleeve to prevent contamination and for shipping purposes. To prevent coring of the needle, a stylet may be concentrically fitted into the through passage of the needle when the needle is inserted into the patient, and removed thereafter.

The forming of the spiral grooves onto the outer circumferential wall of the needle shaft may be accomplished in substantially the same manner as is done for the above-noted Wallace Amniocentesis Needles. In the alternative, the spiral grooves may be formed substantially in accordance with the disclosure of JP2000051219, which was assigned to the assignee of the instant invention. In brief, the '219 publication discloses an edge of a spinning wheel is used to form a groove on a catheter that rotatably moves along a longitudinal direction relative to the wheel.

Inasmuch as the present invention is subject to many variations, modifications and changes in detail, it is intended that the matter described throughout this specification and shown in the accompanying drawings be interpreted as illustrative only, and not in a limiting sense. Accordingly, it is intended that the invention be limited only by the sprit and scope of the hereto appended claims.

The invention claimed is:

1. A method of making an echogenic needle having a shaft that has a sharp distal tip, a proximal end and an outer circumferential surface, comprising:
   positioning relative to the needle a tool adapted to cut a groove having walls orthogonal to each other onto the outer circumferential surface of the needle so that walls having the same length would be formed onto the outer circumferential surface of the needle were the needle to lie along a longitudinal axis relative to the tool at a neutral position;
   repositioning the needle and the tool relative to each other at an angle tilted away from the neutral position toward the proximal end of the needle with the walls remaining orthogonal to each other; and
   rotatably moving the tool and the shaft of the needle relative to each other to cut a spiral groove having a tilt angle relative to the neutral position onto the outer circumferential surface of at least one section of the needle.

2. The method of claim 1, further comprising:
   preferably positioning the tilt angle to be at 10° away from the neutral position.

3. The method of claim 1, further comprising:

forming the spiral groove at multiple sections of the needle.

4. The method of claim 1, further comprising:

forming the spiral groove in one direction along the at least one section of the needle; and rotatably moving the tool and the shaft of the needle relative to each other to form another spiral groove having another tilt angle onto the outer circumferential surface of the needle in another direction along the at least one section such that the spiral groove formed along the one direction and the another spiral groove formed along the another direction crisscross each other.

5. The method of claim 1, further comprising:

forming the spiral groove having the tilt angle to have a pitch of approximately 0.020 in (0.508 mm).

6. The method of claim 1, further comprising:

varying the tilt angle from approximately 5° to 25°.

7. The method of claim 6, further comprising:

forming the spiral groove to have a V-shape.

8. The method of claim 6, further comprising:

forming the spiral groove to have a non-V shape.

9. A method of making an echogenic needle having a shaft including a sharp distal tip and a proximal end with an outer circumferential surface having at least one section thereon adapted to reflect ultrasonic waves directed thereat in a substantially reverse direction, comprising:

positioning relative to the needle a tool adapted to cut a groove having walls orthogonal to each other onto the outer circumferential surface of the needle so that walls having the same length would be formed onto the outer circumferential surface of the needle if the needle were to lie along a longitudinal axis relative to the tool at a neutral position;

repositioning the needle and the tool relative to each other at an angle tilted away from the neutral position toward the proximal end of the needle; and rotatably moving the tool and the shaft of the needle relative to each other to cut a spiral groove having a tilt angle relative to the neutral position onto the outer circumferential surface along the at least one section of the needle with the walls of the groove remaining orthogonal to each other.

10. The method of claim 9, further comprising:

tilting the angle toward the proximal end of the needle from approximately 5° to 25°.

11. The method of claim 9, further comprising:

preferably tilting the angle to be at 10°.

12. The method of claim 9, further comprising:

rotatably moving the tool in another direction relative to the shaft of the needle to form another spiral groove having another angle onto the outer circumferential surface of the needle along another direction different from the direction of the spiral groove such that the spiral groove and the another spiral groove crisscross each other at the at least one section of the needle.

13. The method of claim 12, further comprising:

forming crisscrossing spiral grooves at multiple sections of the needle.

14. The method of claim 9, further comprising:

forming the spiral groove to have a pitch of approximately 0.020 in (0.508 mm).

* * * * *